United States Patent
Rubio Esteban et al.

(10) Patent No.: US 8,071,776 B2
(45) Date of Patent: Dec. 6, 2011

(54) THIENOPYRIDINES AS ALLOSTERIC POTENTIATORS OF THE M4 MUSCARINIC RECEPTOR

(75) Inventors: Almudena Rubio Esteban, Carmel, IN (US); Darryl Wayne Hilliard, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 657 days.

(21) Appl. No.: 11/577,508

(22) PCT Filed: Oct. 18, 2005

(86) PCT No.: PCT/US2005/037271
§ 371 (c)(1),
(2), (4) Date: Dec. 17, 2008

(87) PCT Pub. No.: WO2006/047124
PCT Pub. Date: May 4, 2006

(65) Prior Publication Data
US 2009/0105244 A1    Apr. 23, 2009

Related U.S. Application Data

(60) Provisional application No. 60/621,785, filed on Oct. 25, 2004.

(51) Int. Cl.
*C07D 515/04* (2006.01)
*A61K 31/4365* (2006.01)
(52) U.S. Cl. ..................... 546/114; 514/301
(58) Field of Classification Search ............... 546/144, 546/114; 514/301
See application file for complete search history.

(56) References Cited

U.S. PATENT DOCUMENTS

2004/0180922 A1* 9/2004 Cywin et al. ............. 514/301

FOREIGN PATENT DOCUMENTS
WO WO 01/83472 11/2001

OTHER PUBLICATIONS

Krejci, A. et. al. "Regulation of signal transduction at M2 muscarinic receptor." Physiological Research 2004 53(Suppl. 1), S131-S140.*
Newell, Kelly A et. al. "Opposing short- and long-term effects on muscarinic M1/4 receptor binding following chronic phencyclidine treatment." Journal of Neuroscience Research, 2007, 85(6) 1358-1363.*
Rhea E. Steinpreis "The behavioral and neurochemical effects of phencyclidine in humans and animals: some implications for modeling psychosis" Behavioural Brain Research 1996, 74, 45-55.*
Le Bars, et. al. "Animal Models of Nociception" Pharmacological Reviews 2001, 53, 597-652.*
Gomeza, Jesus et. al.. "Generation and pharmacological analysis of M2 and M4 muscarinic receptor knockout mice." Life Sciences, 2001, 68(22/23), 2457-2466.*
Bymaster, F.P. et al., "Muscarinic mechamisms of antipsychotic atypicality", *Progress in Neuro-Psychopharmacology & Biological Psychiatry*, vol. 27, pp. 1125-1143 (2003).

* cited by examiner

*Primary Examiner* — David K O Dell
(74) *Attorney, Agent, or Firm* — John C. Demeter; Manisha A. Desai

(57) ABSTRACT

The present invention relates to selective allosteric potentiators of the Formula (I):

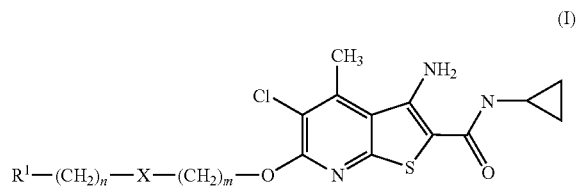

or pharmaceutically acceptable salts thereof, for the treatment of disorders associated with $M_4$ muscarinic receptors.

11 Claims, No Drawings

THIENOPYRIDINES AS ALLOSTERIC POTENTIATORS OF THE M4 MUSCARINIC RECEPTOR

This application is a national phase application under 35 U.S.C. Section 371 for PCT/US2005/037271, filed Oct. 18, 2005, which claims the benefit under 35 U.S.C. Section 119 (e) of U.S. provisional patent application 60/621,785, filed Oct. 25, 2004.

The present invention provides compounds of Formula (I), compositions thereof, and a method for allosteric potentiation of the $M_4$ subtype of muscarinic receptor that comprises administering to a patient an effective amount of a compound of Formula (I). In addition, the present invention relates to processes for preparing the compounds of Formula I and intermediates thereof.

BACKGROUND OF THE INVENTION

The present invention provides compounds that are selective allosteric modulators of the $M_4$ subtype of muscarinic receptor. The $M_4$ muscarinic receptor is believed to play a role in modulating synaptic function in key areas of the brain involved in regulating mood, cravings, attention and cognition. As a result, it provides a novel therapeutic target for the treatment of psychosis; attention disorders, such as attention deficit hyperactivity disorder (ADHD); cognitive disorders, including memory loss; and drug addiction. The $M_2$ and $M_4$ subtypes of muscarinic receptor are also involved in muscarinic agonist-induced analgesic effects, but it is believed that side effects of such treatment are associated primarily with $M_2$ receptor activation. Thus, compounds that selectively modulate $M_4$ receptors would provide a novel treatment strategy for neuropathic pain, without unwanted side effects.

Unlike compounds that act at the neurotransmitter binding site (orthosteric site), allosteric modulators act at a distinct site on the receptor. The use of allosteric modulators provides several advantages in the treatment of disease. Christopoulos, *Nature Reviews* (2002) 1: 198-210. For instance, under saturating conditions (high concentrations of allosteric potentiator) one would not expect excessive stimulation of the $M_4$ muscarinic receptor, since it is dependent on the endogenous neurotransmitter for activation. Second, allosteric agonists exert their physiological effects only in the presence of endogenous agonist. As a result, allosteric potentiators are less likely to produce the condition of receptor desensitization or down-regulation that are associated with excessive cholinergic stimulation. Finally, allosteric modulators are likely to show greater receptor selectivity, especially as the orthosteric binding site is well conserved between muscarinic receptor subtypes.

At present, no selective allosteric modulators of the $M_4$ subtype of muscarinic receptor have been reported. The development of selective $M_4$ allosteric potentiators will therefore greatly enhance the ability to treat disorders such as psychosis and pain, without unwanted side effects. Thus, the present invention provides a class of allosteric modulators of $M_4$ muscarinic receptors, compositions comprising these compounds, and methods of using the compounds.

BRIEF SUMMARY OF THE INVENTION

The invention provides compounds of Formula (I):

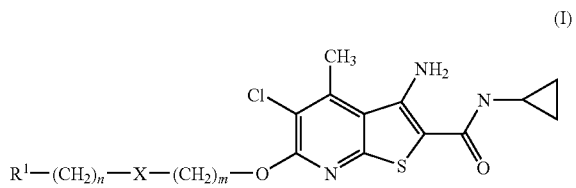

wherein:
m is 1, or 2;
n is 0, 1, or 2;
X is a bond, —O—, —SO$_p$—, —C(O)—, —NR$^2$—, —C(O)—NR$^2$—, or —NR$^2$—C(O)—;
p is 0, 1, or 2;
R$^1$ is hydrogen, hydroxyl, C$_1$-C$_4$ alkyl, phenyl, pyridyl, pyrrolidinyl, piperazinyl, morpholino, thiazolyl, imidazolyl, or 1,3-dioxalanyl;
  which phenyl, piperazinyl, or thiazolyl group may be optionally substituted with one substituent selected from the group consisting of halo or C$_1$-C$_2$ alkyl;
  wherein n cannot be 0 when p is 0, or when X is —O—, —NR$^2$, or —NR$^2$—C(O)—;
R$^2$ is hydrogen or C$_1$-C$_2$ alkyl;
  which C$_1$-C$_2$ alkyl may be optionally substituted with one hydroxyl;
or a pharmaceutically acceptable salt thereof.

The compounds of Formula I are muscarinic receptor potentiators. Specifically, the compounds of Formula I are allosteric potentiators of the $M_4$ subtype of muscarinic receptor. Because these compounds potentiate the physiological effects associated with $M_4$ receptor activation, the compounds are useful in the treatment of disorders related to inadequate $M_4$ receptor activation. These disorders include: pyschosis (particularly, schizophrenia); cognitive disorders (for example, memory loss); attention disorders (such as attention deficit hyperactivity disorder); and pain (in particular, neuropathic pain).

In one embodiment, this invention provides a pharmaceutical composition comprising, as an active ingredient, a compound of Formula I, or a pharmaceutically acceptable salt thereof, in combination with one or more pharmaceutically acceptable carriers, diluents, or excipients.

In a further embodiment, the present invention relates to a method for making a compound represented by Formula I, and intermediates thereof.

In another embodiment, the present invention provides a method for selectively potentiating an $M_4$ receptor by contacting the receptor with a compound of Formula I, or a pharmaceutically acceptable salt thereof.

In another embodiment, the present invention provides methods for treating disorders associated with muscarinic receptors of the $M_4$ subtype, comprising: administering to a patient in need thereof an effective amount of a compound of Formula I. That is, the present invention provides for the use of a compound of Formula I or a pharmaceutical composition thereof for the manufacture of a medicament for the treatment of disorders associated with $M_4$ muscarinic receptors. The present invention also provides a compound of Formula I for use in therapy.

Of the disorders associated with muscarinic $M_4$ receptors, psychosis, pain, attention disorders, and cognitive disorders, such as memory loss, are of particular importance.

Thus, in a preferred embodiment, the present invention provides a method for treating pain, comprising: administering to a patient in need thereof an effective amount of a compound of Formula I, or a pharmaceutically acceptable salt thereof.

In another preferred embodiment, the present invention provides a method for treating psychosis, comprising: administering to a patient in need thereof an effective amount of a compound of Formula I, or a pharmaceutically acceptable salt thereof.

In another preferred embodiment, the present invention provides a method for treating cognitive disorders, comprising: administering to a patient in need thereof an effective amount of a compound of Formula I, or a pharmaceutically acceptable salt thereof.

DETAILED DESCRIPTION OF THE INVENTION

The terms and abbreviations used in the preparations and examples have their normal meanings unless otherwise designated. For example "° C." refers to degrees Celsius; "N" refers to normal or normality; "mol" refers to mole or moles; "h" refers to hour(s); "eq" refers to equivalent; "g" refers to gram or grams; "L" refers to liter or liters; "M" refers to molar or molarity; "brine" refers to a saturated aqueous sodium chloride solution; "J" refers to hertz; "ES" refers to electrospray; "MS" refers to mass spectrometry; "NMR" refers to nuclear magnetic resonance spectroscopy; "TLC" refers to thin layer chromatography; "ACN" refers to acetonitrile; "DMF" refers to N,N-dimethylformamide; "DMSO" refers to dimethylsulfoxide; "Et$_2$O" refers to diethyl ether; "EtOAc" refers to ethyl acetate; "MeOH" refers to methanol; "EtOH" refers to ethanol; "iPrOH" refers to isopropanol; "TEA" refers to triethylamine; "TFA" refers to trifluoroacetic acid; "THF" refers to tetrahydrofuran.

As used herein, the term "$C_1$-$C_4$ alkyl" refers to straight or branched, monovalent, saturated aliphatic chains of 1 to 4 carbon atoms and includes, but is not limited to, methyl, ethyl, propyl, isopropyl, butyl, isobutyl, sec-butyl, and tert-butyl. The terms "$C_1$-$C_3$ alkyl" and "$C_1$-$C_2$ alkyl" are encompassed within the definition of "$C_1$-$C_4$ alkyl."

"Halo," "halogen," and "halide" represent a chloro, fluoro, bromo or iodo atom. Preferred halogens include chloro and fluoro.

It will be clear to the person of skill in the art that when X is —NR$^2$—C(O)—, the compound of Formula (I) is as depicted below:

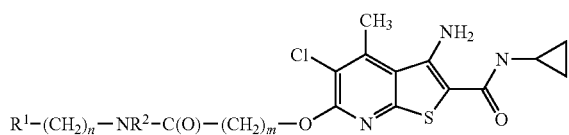

Certain compounds of the present invention may exist as stereoisomers. The Cahn-Prelog-Ingold designations of (R)- and (S)- and the designations of L- and D- for stereochemistry relative to the isomers of glyceraldehyde are used herein to refer to specific isomers. The specific stereoisomers can be prepared by stereospecific synthesis or can be resolved and recovered by techniques known in the art, such as chromatography on chiral stationary phases, and fractional recrystallization of addition salts formed by reagents used for that purpose. Useful methods of resolving and recovering specific stereoisomers are known in the art and described in E. L. Eliel and S. H. Wilen, *Stereochemistry of Organic Compounds*, (Wiley-Interscience 1994), and J. Jacques, A. Collet, and S. H. Wilen, *Enantiomers, Racemates, and Resolutions*, Wiley-Interscience 1981). It is understood that the present invention contemplates all enantiomers and mixtures of enantiomers, including racemates.

The skilled artisan will recognize that certain compounds of the present invention may exist as tautomers. It is understood that tautomeric forms of the compounds of Formula (I) are also encompassed in the present invention.

This invention includes the pharmaceutically acceptable salts of the compounds of Formula I. A compound of this invention can possess a sufficiently basic functional group, which can react with any of a number of inorganic and organic acids, to form a pharmaceutically acceptable salt.

The term "pharmaceutically-acceptable salt" as used herein, refers to a salt of a compound of the above Formula I. It should be recognized that the particular counterion forming a part of any salt of this invention is usually not of a critical nature, so long as the salt as a whole is pharmacologically acceptable and as long as the counterion does not contribute undesired qualities to the salt as a whole.

The compounds of Formula I and the intermediates described herein form pharmaceutically-acceptable acid addition salts with a wide variety of organic and inorganic acids and include the physiologically-acceptable salts which are often used in pharmaceutical chemistry. Such salts are also part of this invention. A pharmaceutically-acceptable acid addition salt is formed from a pharmaceutically-acceptable acid, as is well known in the art. Such salts include the pharmaceutically acceptable salts listed in *Journal of Pharmaceutical Science*, 66, 2-19 (1977), which are known to the skilled artisan. See also, The Handbook of Pharmaceutical Salts; Properties, Selection, and Use. P. H. Stahl and C. G. Wermuth (ED.s), Verlag, Zurich (Switzerland) 2002.

Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartarate, and the like.

As used herein, the term "patient" refers to a mammal that is afflicted with one or more disorders associated with $M_4$ receptors. Guinea pigs, dogs, cats, rats, mice, horses, cattle, sheep, and humans are examples of mammals within the scope of the meaning of the term. It will be understood that the most preferred patient is a human.

It is also recognized that one skilled in the art may affect the disorders by treating a patient presently afflicted with the disorders or by prophylactically treating a patient afflicted with the disorders with an effective amount of the compound of Formula I. Thus, the terms "treatment" and "treating" are intended to refer to all processes wherein there may be a slowing, interrupting, arresting, controlling, or stopping of the progression of the disorders described herein, and is intended to include prophylactic treatment of such disorders, but does not necessarily indicate a total elimination of all disorder symptoms.

As used herein, the term "effective amount" of a compound of Formula I refers to an amount that is effective in treating the disorders described herein.

As with any group of pharmaceutically active compounds, some groups are preferred in their end use application. Preferred embodiments of the present invention are discussed below.

(a) m is 1;
(b) m is 2;
(c) n is 0;
(d) n is 1;
(e) n is 2;
(f) X is a bond;
(g) X is —C(O)—$NR^2$—;
(h) X is —O—;
(i) $R^1$ is hydrogen;
(j) $R^1$ is hydroxyl;
(k) $R^1$ is $C_1$-$C_4$ alkyl;
(l) $R^1$ is pyridyl;
(m) $R^1$ is piperazinyl;
(n) $R^1$ is morpholino;
(o) $R^2$ is hydrogen;

Preferred compounds of the present invention include: 3-amino-5-chloro-6-methoxy-4-methyl-thieno[2,3-b]pyridine-2-carboxylic acid cyclopropylamide; 3-Amino-5-chloro-4-methyl-6-(2-morpholin-4-yl-ethoxy)-thieno[2,3-b]pyridine-2-carboxylic acid cyclopropylamide.

The skilled artisan will appreciate that additional preferred embodiments may be selected by combining the preferred embodiments above, or by reference to the examples given herein.

Schemes

The compounds disclosed herein can be made according to the following schemes. The schemes, preparations, and examples should in no way be understood to be limiting in any way as to how the compounds may be made.

The skilled artisan will appreciate that the introduction of certain substituents will create asymmetry in the compounds of Formula (I). The present invention contemplates all stereoisomers, enantiomers, and mixtures of enantiomers, including racemates and diastereomers. It is preferred that the compounds of the invention containing chiral centers are single enantiomers.

It will be recognized by one of skill in the art that the individual steps in the following schemes may be varied to provide the compounds of Formula (I). The particular order of steps required to produce the compounds of Formula (I) is dependent upon the particular compound being synthesized, the starting compound, and the relative lability of the substituted moieties. Some substituents have been eliminated in the following schemes for the sake of clarity and are not intended to limit the teaching of the schemes in any way.

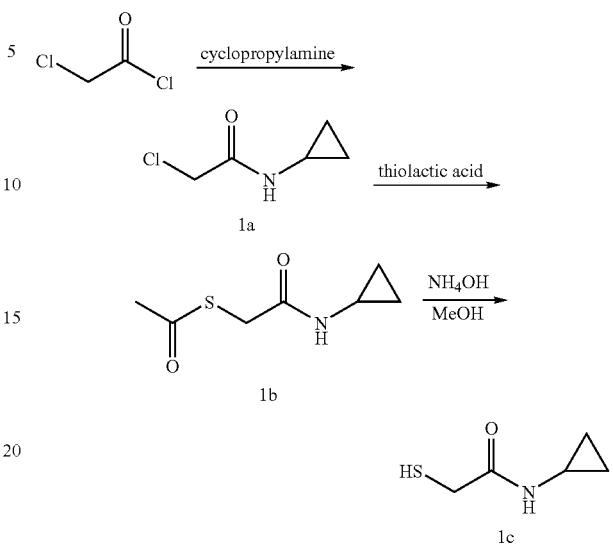

In the first synthetic campaign (Scheme I), chloroacetyl chloride is reacted with cyclopropylamine in the presence of a base, e.g., TEA or pyridine, in an aprotic solvent, e.g., diethylether or methylene chloride, at temperatures ranging from 0° C. to room temperature, to give the intermediate amide Compound Ia. Compound Ia is treated with thiolactic acid and a base, e.g., TEA in a polar aprotic solvent, e.g., dichloromethane to give the intermediate amide Compound 1b. Compound 1b is hydrolyzed in a lower ($C_1$-$C_4$) alkanol, e.g., MeOH, and concentrated ammonium hydroxide solution from 0° C. to room temperature to give the thiol reagent Compound 1c. The product can be isolated and purified by techniques well known in the art, such as precipitation, filtration, extraction, evaporation trituration, chromatography, and recrystallization.

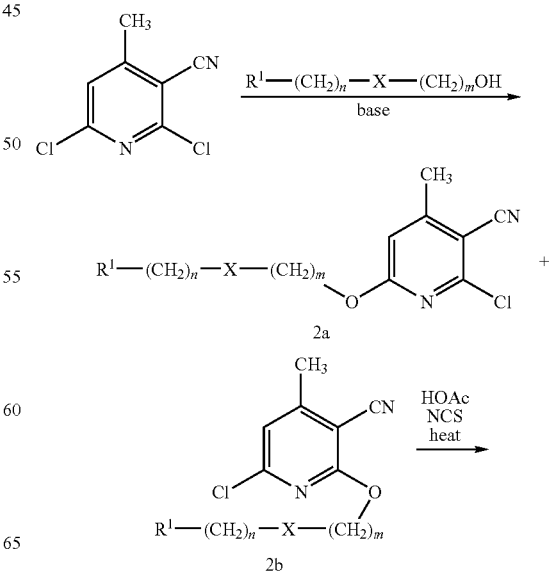

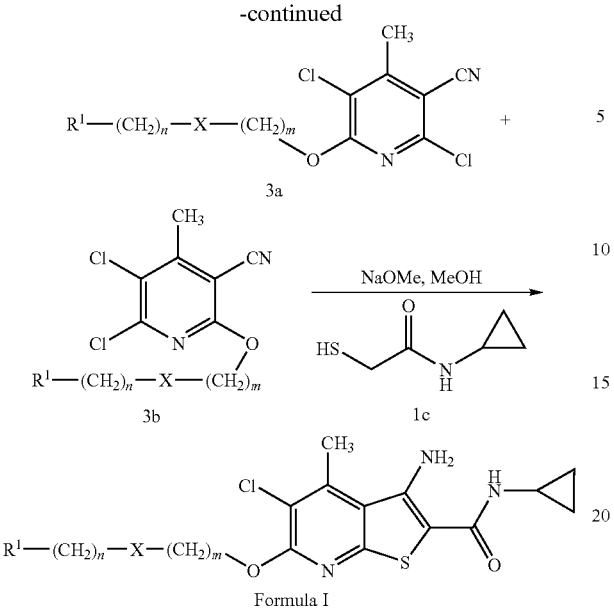

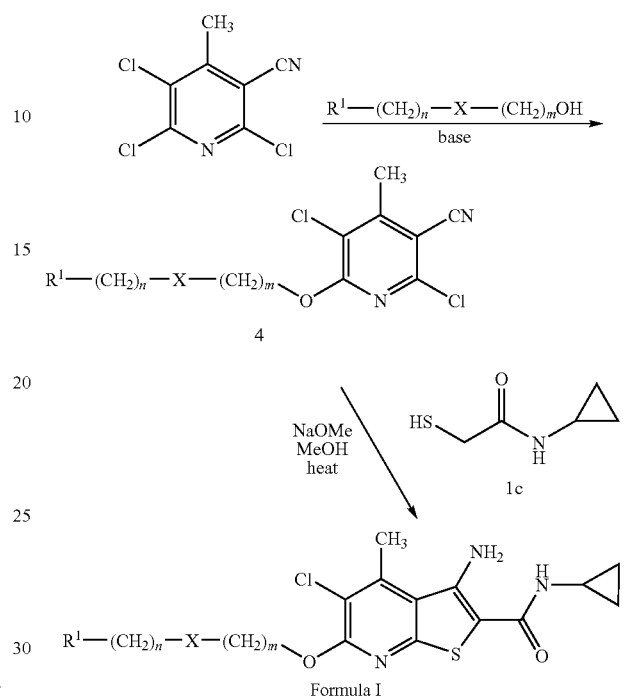

In another synthetic campaign of Scheme II, 2,5-dichloro-4-methyl-nicotinonitrile is treated with an alkoxide anion, generated from an alkanol and a base, e.g., sodium hydride or lithium bis(trimethylsilyl)amide in alkanol solvent from 0° C. up to room temperature for a reaction time ranging from 30 min to 24 h, to give a mixture of displacement products 2a and 2b. The mixture 2a & 2b is chlorinated with 2-4 equivalents of N-chlorosuccinimide in glacial acetic acid from 100 to 140° C. in a sealed reaction vessel for 24 to 48 h to give the chlorinated intermediate mixture 3a and 3b. The chlorinated mixture 3a and 3b is treated with Compound 1c in the presence of a suitable base, such as sodium alkoxide, potassium alkoxide, or lithium alkoxide, wherein the alkoxide is a lower molecular weight alkoxide. The base is in an alkanol, such as methanol. A preferred base in alkanol solution is sodium methoxide in MeOH. The reaction is carried out at 100 to 140° C. in a sealed reaction vessel for 30 min to 4 h to produce the compound of Formula I. The product can be isolated and purified by techniques described above.

In Scheme III, 4-methyl-2,5,6-trichloro-nicotinonitrile is treated with an alkoxide anion, generated from an alkanol and a base, e.g., sodium hydride or lithium bis(trimethylsilyl)amide in alkanol solvent from 0° C. up to room temperature from 30 min to 24 h to give a displacement product 4. The intermediate 4 is treated with reagent Compound 1c as in Scheme I to give Formula I. The product can be isolated and purified by techniques described above.

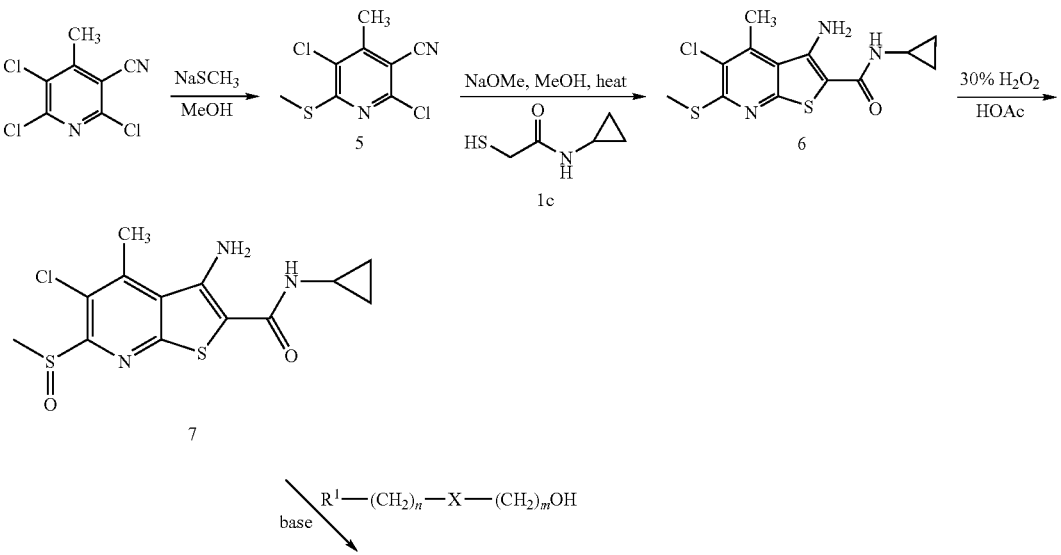

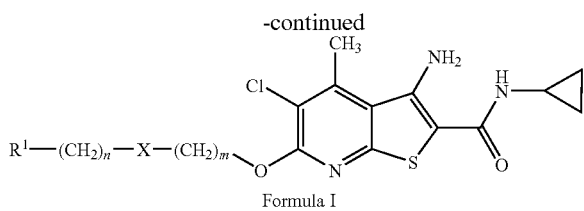

Formula I

In Scheme IV, 4-methyl-2,5,6-trichloro-nicotinonitrile is treated with a lower molecular weight lithium, sodium, or potassium thioalkoxide ($C_1$-$C_4$) such as sodium thiomethoxide in a lower molecular weight alkanol ($C_1$-$C_4$), such as MeOH, to give the displacement product 5. Intermediate 5 is reacted with Compound 1c of Scheme I to give Compound 6. Compound 6 is oxidized with, e.g., hydrogen peroxide in a lower molecular weight alkanol ($C_1$-$C_4$), such as MeOH, from room temperature to 40° C. and from 12 to 48 b to give the sulfoxide 7. Displacement of sulfoxide 7 by an alkoxide in alkanol, as in Schemes I or II, gives compounds of Formula I. The product can be isolated and purified by techniques described above.

EXAMPLES

Example 1

3-Amino-5-chloro-6-methoxy-4-methyl-thieno[2,3-b]pyridine-2-carboxylic acid cyclopropylamide

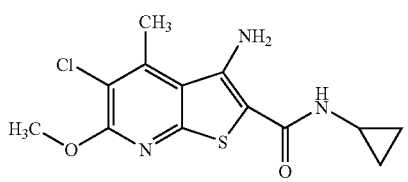

A. 2-Chloro-N-cyclopropyl-acetamide

To a solution of cyclopropylamine (50.0 g, 0.876 mol) in dichloromethane (700 ml) at 0° C. is added 2-chloroacetyl chloride (49.4 g, 0.436 mol) dropwise by addition funnel. The resulting mixture is stirred at 0° C. for 2 hours, then filtered through a pad of Celite®. The filtrate is concentrated to an orange solid, which is slurried in 500 ml of hexane, then filtered. The collected orange solid is dried under house vacuum for 30 minutes. This gives the title compound as an orange solid (58.12 g, 99%). Mass (m/z): 134.1 ($M^+$+1).

B. Thioacetic acid S-cyclopropylcarbamoylmethyl ester

To a solution of 2-chloro-N-cyclopropyl-acetamide (58.1 g, 0.435 mol) in dichloromethane (700 ml) at 0° C. is added thiolactic acid (49.65 g, 0.652 mol). The mixture is stirred at 0° C. for 5 minutes, then TEA (88.0 g, 0.870 mol) is added very slowly (exothermic reaction). The mixture is stirred at 0° C. for 2 hours, then poured over 700 ml of water with stirring. The aqueous layer is acidified to pH2 with 5 N HCl, and the layers are shaken and separated. The aqueous layer is extracted with dichloromethane (2×400 ml). The combined organic layers are washed with brine, then dried (anhydrous magnesium sulfate), filtered, and concentrated to give the title compound as a yellow-orange solid (74.5 g, 99%). Mass (m/z): 174.1 ($M^+$+1).

C. N-Cyclopropyl-2-mercapto-acetamide

To a solution of thioacetic acid S-cyclopropylcarbamoyl-methyl ester (17.0 g, 98.14 mmol) in MeOH (200 ml) is added a 28% solution of ammonium hydroxide in water (17 ml). The resulting solution is stirred at room temperature for 1 hour. The reaction solution is poured over water (400 ml) and acidified to pH2 with 5N HCl. The solution is extracted with EtOAc (6×200 ml) and the combined organic layers are dried (anhydrous magnesium sulfate), filtered, and concentrated to give the title compound as a light orange solid (12.87 g, 99%). Mass (m/z): 132.1 ($M^+$1).

D. 2,5-Dichloro-6-methoxy-4-methyl-nicotinonitrile

To a slurry of 2,5,6-trichloro-4-methyl-nicotinonitrile (11.0 g, 49.67 mmol, Tetrahedron, 1977, 33, 113-117) in MeOH (125 ml) is added sodium methoxide solution (25% wt. in MeOH)(11.92 ml, 52.15 mmol). The reaction mixture is stirred at 0° C. for 30 minutes, then room temperature for 1 hour. The reaction is quenched by the addition of water (300 ml) and a thick, white precipitate is formed. An additional 200 ml of water is added and the mixture is stirred at 0° C. for 10 minutes. The precipitate is collected by filtration and dried (vacuum oven for 16 hours at 60° C.) to give the title compound as an off-white solid (10.05 g, 93%). Mass (m/z): 217.0 ($M^+$+1).

E. 3-Amino-5-chloro-6-methoxy-4-methyl-thieno[2,3-b]pyridine-2-carboxylic acid cyclopropylamide To a solution of N-cyclopropyl-2-mercapto-acetamide (6.65 g, 50.68 mmol) in MeOH (100 ml), is added sodium methoxide solution (25% wt. in MeOH)(11.59 ml, 50.68 mmol). The resulting solution is stirred at room temperature for 10 minutes, and then treated with 2,5-dichloro-6-methoxy-4-methyl-nicotinonitrile (10.0 g, 46.07 mmol). The reaction vessel is sealed and heated at 100° C. for 2 hours. The reaction mixture is cooled to room temperature and poured over 500 ml of cold water. A thick white precipitate is formed. The mixture is stirred at 0° C. for 10 minutes, then the solid is collected by filtration. The fluffy white solid (title compound) is placed in the vacuum oven at 60° C. to dry overnight (7.74 g, 54%). Mass (m/z): 312.0 ($M^+$+1).

Example 2

3-Amino-5-chloro-6-hydroxy-4-methyl-thieno[2,3-b]pyridine-2-carboxylic acid cyclopropylamide

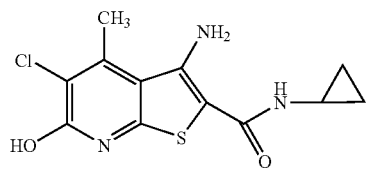

To a solution of 3-amino-5-chloro-6-methoxy-4-methyl-thieno[2,3-b]pyridine-2-carboxylic acid cyclopropylamide (5.0 g, 16.04 mmol) in DMF (45 ml) is added solid 95% sodium thiomethoxide (1.30 g, 17.64 mmol). The reaction vessel is sealed and heated at 100° C. for 5 hours. The reaction is cooled to room temperature and quenched by the addition of water (75 ml). The mixture is acidified to pH2 by the addition of 5N HCl. Gradually, a thick, white precipitate is formed, which is stirred at 0° C. for 10 minutes, then collected by filtration. The solid is dried in the vacuum oven overnight at 60° C. to afford the title compound as a white solid (4.13 g, 86%). Mass (m/z): 298.0 (M$^+$+1).

Example 3

3-Amino-5-chloro-6-isopropoxy-4-methyl-thieno[2,3-b]pyridine-2-carboxylic acid cyclopropylamide

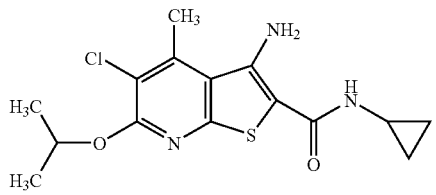

A. 1:1 Mixture of 2-chloro-6-isopropoxy-4-methyl-nicotinonitrile and 6-chloro-2-isopropoxy-4-methyl-nicotinonitrile To a slurry of 2,6-dichloro-4-methylnicotinonitrile (0.500 g, 2.67 mmol) in 4 mls of 2-propanol at 0° C. is added dropwise a solution of lithium bis(trimethylsilyl)amide (1.0 M in hexanes) (2.67 ml, 2.67 mmol). The resulting mixture is stirred at 0° C. for 20 minutes, then room temperature for 5 hours. The reaction is quenched by the addition of water (10 ml). The mixture is partitioned between water and EtOAc (75 ml each), and the layers are shaken and separated. The organic layer is washed with brine, then dried (anhydrous magnesium sulfate), filtered, and concentrated to give the title compound (tan solid, 0.510 g, 91% yield) as a 1:1 mixture of regioisomers (based on NMR data). Mass (m/z): 211.0 (M$^+$+1).

B. 1:1 Mixture of 2,5-dichloro-6-isopropoxy-4-methyl-nicotinonitrile and 5,6-dichloro-2-isopropoxy-4-methyl-nicotinonitrile To a thick-glassed, screw top reaction tube are added a 1:1 mixture of 2-chloro-6-isopropoxy-4-methyl-nicotinonitrile and 6-chloro-2-isopropoxy-4-methyl-nicotinonitrile (0.510 g, 2.42 mmol), glacial acetic acid (7 ml), and N-chlorosuccinimide (1.29 g, 9.68 mmol). The reaction tube is sealed, and the mixture is heated at 125° C. for 48 hours. The reaction mixture is cooled to room temperature and partitioned between water and EtOAc (100 ml each). The layers are shaken and separated. The organic layer is washed successively with saturated aqueous sodium bicarbonate solution (100 ml), water (100 ml), and brine (100 ml). The organic layer is dried (anhydrous magnesium sulfate), filtered, and concentrated to give a brown oil. Flash chromatography (5:1 hexane: EtOAc) affords the title compound (white solid, 0.400 g, 67% yield) as a 1:1 mixture of regioisomers (based on NMR data). Mass (m/z): 243.0 (M$^+$−1).

C. 3-amino-5-chloro-6-isopropoxy-4-methyl-thieno[2,3-b]pyridine-2-carboxylic acid cyclopropylamide To a solution of N-cyclopropyl-2-mercapto-acetamide (0.498 g, 3.80 mmol) in MeOH (5 ml) is added sodium methoxide solution (25% wt. in MeOH)(0.652 ml, 2.85 mmol). The resulting solution is stirred at room temperature for 30 minutes, then treated with a 1:1 mixture of 2,5-dichloro-6-isopropoxy-4-methyl-nicotinonitrile and 5,6-dichloro-2-isopropoxy-4-methyl-nicotinonitrile (0.400 g, 1.63 mmol). The reaction vessel is sealed, heated at 100° C. for 2.5 hours, and cooled to room temperature. The reaction mixture is poured over water (60 ml), then extracted with EtOAc (2×40 ml). The combined organic layers are washed with brine (50 ml), dried (anhydrous magnesium sulfate), filtered, and concentrated to give a yellow-brown solid. Flash chromatography (1.5:1 hexane:EtOAc) affords the title compound as a tan solid (20 mg). Mass (m/z): 340.1 (M$^+$+1).

Example 4

3-Amino-5-chloro-6-(2-methoxy-ethoxy)-4-methyl-thieno[2,3-b]pyridine-2-carboxylic acid cyclopropylamide

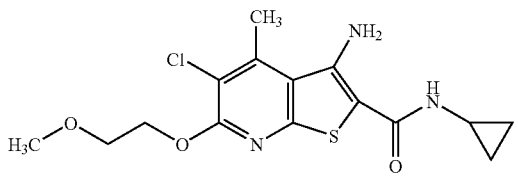

A. 1:1 Mixture of 2-chloro-6-(2-methoxy-ethoxy)-4-methyl-nicotinonitrile and 6-chloro-2-(2-methoxy-ethoxy)-4-methyl-nicotinonitrile To a slurry of 2,6-dichloro-4-methylnicotinonitrile (0.500 g, 2.67 mmol) in 6 mls of 2-methoxymethanol at 0° C. is added dropwise a solution of lithium bis(trimethylsilyl) amide (1.0 M in hexanes)(2.67 ml, 2.67 mmol). The resulting mixture is stirred at 0° C. for 20 minutes, then room temperature for 5 hours. The reaction is quenched by the addition of water (10 ml). The mixture is partitioned between water and EtOAc (75 ml each), and the layers are shaken and separated. The organic layer is washed with brine, then dried (anhydrous magnesium sulfate), filtered, concentrated, and flashed (5:1 hexane:EtOAc) to give the title compound (white solid, 0.530 g, 88% yield) as a 1:1 mixture of regioisomers (based on NMR data). Mass (m/z): 227.0 (M$^+$+1).

B. 1:1 Mixture of 2,5-dichloro-6-(2-methoxy-ethoxy)-4-methyl-nicotinonitrile and 5,6-dichloro-2-(2-methoxy-ethoxy)-4-methyl-nicotinonitrile To a thick-glassed, screw top reaction tube are added a 1:1 mixture of 2-chloro-6-(2-methoxy-ethoxy)-4-methyl-nicotinonitrile and 6-chloro-2-(2-methoxy-ethoxy)-4-methyl-nicotinonitrile (0.450 g, 1.99 mmol), glacial acetic acid (8 ml), and N-chlorosuccinimide (1.06 g, 7.94 mmol). The reaction tube is sealed, and the mixture is heated at 110° C. for 24 hours. The reaction mixture is cooled to room temperature and partitioned between water and EtOAc (100 ml each). The layers are shaken and separated. The organic layer is washed successively with saturated aqueous sodium bicarbonate solution (3×50 ml) and water (100 ml). The organic layer is dried (anhydrous magnesium sulfate), filtered, and concentrated to give the title compound as a yellow-orange oil (0.453 g, 87% yield) in a 1:1 mixture of regioisomers (based on NMR data). Mass (m/z): 261.0 (M$^+$−1).

C. 3-Amino-5-chloro-6-(2-methoxy-ethoxy)-4-methyl-thieno[2,3-b]pyridine-2-carboxylic acid cyclopropylamide To a solution of N-cyclopropyl-2-mercapto-acetamide (0.452 g, 3.45 mmol) in MeOH (5 ml) is added sodium methoxide solution (25% wt. in MeOH)(0.589 ml, 2.58 mmol). The resulting solution is stirred at room temperature for 30 minutes, then treated with a 1:1 mixture of 2,5-dichloro-6-(2-methoxy-ethoxy)-4-methyl-nicotinonitrile and 5,6-dichloro-2-(2-methoxy-ethoxy)-4-methyl-nicotinonitrile (0.450 g, 1.72 mmol). The reaction vessel is sealed, heated at 100° C. for 2.5 hours, and cooled to room temperature. The reaction mixture is poured over water (60 ml), then extracted with EtOAc (2×40 ml). The combined organic layers are washed with brine (50 ml), dried (anhydrous magnesium sulfate), filtered, and concentrated to give a yellow-brown solid. Flash chromatography (1.5:1 hexane:EtOAc) affords the title compound as a cream colored solid (53 mg, 10%). Mass (m/z): 356.1 (M$^+$+1).

Example 5

3-Amino-5-chloro-6-(2-hydroxy-ethoxy)-4-methyl-thieno[2,3-b]pyridine-2-carboxylic acid cyclopropylamide

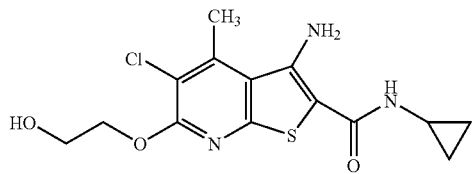

A. 2,5-Dichloro-4-methyl-6-methylsulfanyl-nicotinonitrile

To a slurry of 2,5,6-trichloro-4-methyl-nicotinonitrile (10.0 g, 45.2 mmol, *Tetrahedron*, 1977, 33, 113-117) in MeOH (150 ml) at 0° C. is added solid sodium thiomethoxide (3.33 g, 45.2 mmol). The mixture is stirred at 0° C. for 1 hour, then room temperature for 1 hour. The reaction is quenched by the addition of water (250 ml). The mixture is partitioned between water and EtOAc (500 ml each), and the layers are shaken and separated. The organic layer is dried (anhydrous magnesium sulfate), filtered, and concentrated to give the title compound as a yellow solid (10.5 g, 99%). Mass (m/z): 233.0 (M$^+$+1).

B. 3-Amino-5-chloro-4-methyl-6-methylsulfanyl-thieno[2,3-b]pyridine-2-carboxylic acid cyclopropylamide To a mixture of thioacetic acid S-cyclopropylcarbamoyl-methyl ester (8.58 g, 49.5 mmol) and MeOH (100 ml) is added sodium methoxide solution (25% wt. in MeOH)(15.4 ml, 67.5 mmol). The resulting solution is stirred at room temperature for 20 minutes, then treated with 2,5-dichloro-4-methyl-6-methylsulfanyl-nicotinonitrile (10.5 g, 45.0 mmol). The mixture is refluxed at 100° C. for 2 hours, cooled to room temperature, and quenched by adding water (100 ml). The mixture is partitioned between water and EtOAc (300 ml each), and the layers are shaken and separated. The aqueous layer is extracted with EtOAc (2×150 ml). The combined organic layers are washed with brine (200 ml), dried (anhydrous magnesium sulfate), filtered, and concentrated to give an orange solid. Flash chromatography (1:1 hexane:EtOAc) affords the title compound as a yellow solid (8.4 g, 57%). Mass (m/z): 328.1 (M$^+$+1).

C. 3-Amino-5-chloro-6-methanesulfinyl-4-methyl-thieno[2,3-b]pyridine-2-carboxylic acid cyclopropylamide To a slurry of 3-amino-5-chloro-4-methyl-6-methylsulfanyl-thieno[2,3-b]pyridine-2-carboxylic acid cyclopropylamide (7.5 g, 22.87 mmol) in glacial acetic acid (75 ml) is added a solution of 30% hydrogen peroxide in water (2.85 ml, 25.16 mmol). The mixture is stirred at 35° C. for 16 hour, cooled to room temperature, and poured over water (300 ml). A bright yellow precipitate is formed. The mixture is stirred at 0° C. for 1 hour then the solid is collected by filtration and dried under vacuum at 60° C. for 3 hours to afford the title compound as a bright yellow solid (5.58 g, 71%). Mass (m/z): 344.1 (M$^+$+1).

D. (3-Amino-5-chloro-2-cyclopropylcarbamoyl-4-methyl-thieno[2,3-b]pyridin-6-yloxy)-acetic acid methyl ester To a solution of methyl glycolate (6.55 g, 72.7 mmol) in THF (35 ml) at room temperature is added dropwise a solution of lithium bis(trimethylsilyl)amide (1.0 M in hexanes) (36.35 ml, 36.35 mmol). The resulting mixture is stirred for 20 minutes, then treated with 3-amino-5-chloro-6-methanesulfinyl-4-methyl-thieno[2,3-b]pyridine-2-carboxylic acid cyclopropylamide (5.0 g, 14.54 mmol). The reaction vessel is sealed and heated at 90° C. for 3 hours. The reaction is cooled to room temperature and quenched by the addition of water (50 ml). The mixture is partitioned between water and EtOAc (250 ml each), and the layers are shaken and separated. The aqueous layer is extracted with 2×100 ml of EtOAc. The combined organic layers are dried (anhydrous magnesium sulfate), filtered, concentrated, and flashed (1:1 hexane:EtOAc) to give the title compound as a yellow solid (3.1 g, 58%). Mass (m/z): 370.1 (M$^+$+1), 368.0 (M$^+$−1).

E. 3-Amino-5-chloro-6-(2-hydroxy-ethoxy)-4-methyl-thieno[2,3-b]pyridine-2-carboxylic acid cyclopropylamide To a solution of (3-amino-5-chloro-2-cyclopropylcarbamoyl-4-methyl-thieno[2,3-b]pyridin-6-yloxy)-acetic acid methylester (0.250 g, 0.676 mmol) in THF (3 ml) at −78° C. is added dropwise a solution of diisobutylaluminum hydride (1.5M in toluene)(1.35 ml, 2.03 mmol). The reaction solution is stirred at −78° C. for 30 minutes, then room temperature for 1 hour. If the reaction is not complete, according to TLC (2:1 EtOAc:hexane), an additional 1.0 eq of diisobutylaluminum hydride (1.5M in toluene)(0.45 ml, 0.676 mmol) may be added. After 15 minutes, the reaction is quenched by the addition of 3 ml of a 1:1 mixture of MeOH:water. The reaction mixture is partitioned between water and EtOAc (50 ml each), and the layers are shaken and separated. The aqueous layer is extracted with 2×50 ml of EtOAc, and the combined organic layers are dried (anhydrous magnesium sulfate), filtered, and concentrated to give a yellow solid. This solid is taken up in 2:1 EtOAc:hexane, and once dissolved, a yellow precipitate is formed. The yellow solid is collected by filtration and dried in the vacuum oven at 60° C. overnight to afford the title compound as a yellow solid (0.155 g, 67%). Mass (m/z): 342.1 (M$^+$+1).

Example 6

3-Amino-5-chloro-4-methyl-6-(2-morpholin-4-yl-ethoxy)-thieno[2,3-b]pyridine-2-carboxylic acid cyclopropylamide

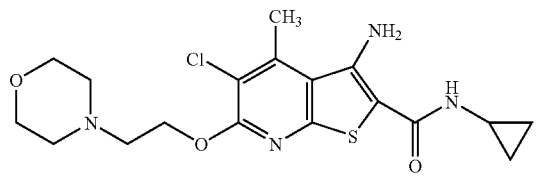

To a solution of 4-(2-hydroxyethyl)morpholine (5.72 g, 43.62 mmol) in THF (25 ml) at room temperature is added dropwise a solution of lithium bis(trimethylsilyl)-amide (1.0 M in hexanes) (21.80 ml, 21.80 mmol). The reaction mixture is stirred for 15 minutes, and then is treated with 3-amino-5-chloro-6-methanesulfinyl-4-methyl-thieno[2,3-b]pyridine-2-carboxylic acid cyclopropylamide (30 g, 8.72 mmol). The reaction vessel is sealed and heated at 80° C. for 3 hours. The reaction is cooled to room temperature and quenched by the addition of water (200 ml). A yellow precipitate is formed. The mixture is diluted to 350 ml with water and cooled to 0° C. The yellow precipitate is collected by filtration. The solid is slurried in 100 ml of 3:1 hexane:EtOAc and stirred for 10 minutes. The mixture is filtered, and the collected solid is dried in the vacuum oven overnight to afford the title compound as a yellow solid (2.11 g, 59%). Mass (m/z): 411.1 (M$^+$+1), 409.1 (M$^+$−1).

Example 7

3-Amino-5-chloro-4-methyl-6-[2-(4-methyl-thiazol-5-yl)-ethoxy]-thieno[2,3-b]pyridine-2-carboxylic acid cyclopropylamide

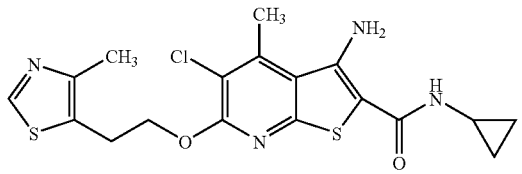

To a solution of 4-methyl-5-thiazole-ethanol (0.375 g, 2.62 mmol) in THF (1 ml) at room temperature is added dropwise a solution of lithium bis(trimethylsilyl)amide (1.0M in hexanes)(1.74 ml, 1.74 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.300 g, 0.872 mmol). The reaction mixture is stirred at room temperature for 18 hours, then quenched by the addition of water (5 ml). The mixture is partitioned between water and EtOAc (40 ml each). Five ml of 1 N HCl is added, and the layers are shaken and separated. The aqueous layer is extracted with EtOAc (50 ml) and the combined organic layers are dried (anhydrous magnesium sulfate), filtered, concentrated, and flashed (1:2 hexane:EtOAc) to give the title compound as a pale yellow solid (0.094 g, 25%). Mass (m/z): 423.1 (M++1), 421.1 (M$^+$−1).

Example 8

(3-Amino-5-chloro-2-cyclopropylcarbamoyl-4-methyl-thieno[2,3-b]pyridin-6-yloxy)-acetic acid dimethylamide

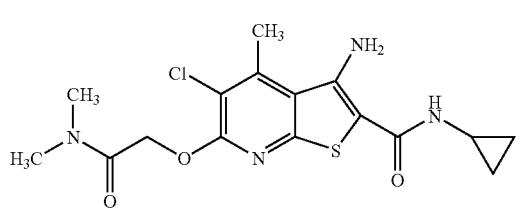

A. (3-Amino-5-chloro-2-cyclopropylcarbamoyl-4-methyl-thieno[2,3-b]pyridin-6-yloxy)-acetic acid To a solution of (3-amino-5-chloro-2-cyclopropylcarbamoyl-4-methyl-thieno[2,3-b]pyridin-6-yloxy)-acetic acid methyl ester (0.940 g, 2.54 mmol) in THF (20 ml) is added 95% potassium trimethylsilanolate (1.63 g, 12.71 mmol). The resulting mixture is stirred at room temperature for 2 hours and then quenched by the addition of water (50 ml). The mixture is acidified to pH2 by the addition of 1 N HCl, and then extracted with EtOAc (100 ml). The organic layer is washed with brine (40 ml), then dried (anhydrous magnesium sulfate), filtered, and concentrated to give the title compound as a yellow solid (0.693 g, 77%). Mass (m/z): 355.9 (M$^+$+1), 354.0 (M$^+$−1).

B. (3-Amino-5-chloro-2-cyclopropylcarbamoyl-4-methyl-thieno[2,3-b]pyridin-6-yloxy)-acetic acid dimethylamide To a solution of (3-amino-5-chloro-2-cyclopropylcarbamoyl-4-methyl-thieno[2,3-b]pyridin-6-yloxy)-acetic acid (0.200 g, 0.562 mmol) in a 1:1 mixture of THF:DMF (1.5 ml each) are added 1-hydroxybenzotriazole hydrate (0.099 g, 0.731 mmol), N,N-diisopropylethylamine (0.109 g, 0.843 mmol), 1-[3-(dimethylamino)-propyl]-3-ethylcarbodiimide hydrochloride (0.162 g, 0.843 mmol), and dimethylamine (2.0 M in MeOH)(0.85 ml, 1.69 mmol). The resulting solution is stirred at room temperature for 24 hours, then at 50° C. for 24 hours. The reaction is cooled to room temperature and quenched by the addition of water. The mixture is partitioned between water and EtOAc (40 ml each), and the layers are shaken and separated. The aqueous layer is acidified to pH 3 with 1 N HCl and then extracted with EtOAc (40 ml). The combined organic layers are dried (anhydrous magnesium sulfate), filtered, concentrated, and flashed (100% EtOAc) to give the title compound as a white solid (0.040 g, 19%). Mass (m/z): 383.2 (M⁺+1), 381.2 (M⁺−1).

Example 9

(3-Amino-5-chloro-2-cyclopropylcarbamoyl-4-methyl-thieno[2,3-b]pyridin-6-yloxy)-acetic acid 2-hydroxyethylamide

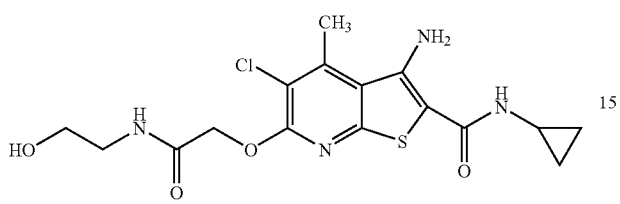

To a solution of (3-amino-5-chloro-2-cyclopropylcarbamoyl-4-methyl-thieno[2,3-b]pyridin-6-yloxy)-acetic acid (0.200 g, 0.562 mmol) in a 1:1 mixture of THF:DMF (1.5 ml each) are added 1-hydroxybenzotriazole hydrate (0.099 g, 0.73 mmol), N,N-diisopropylethylamine (0.109 g, 0.843 mmol), 1-[3-(dimethylamino)-propyl]-3-ethylcarbodiimide hydrochloride (0.162 g, 0.843 mmol), and ethanolamine (0.103 g, 1.69 mmol). The resulting solution is stirred at room temperature for 24 hours, then at 50° C. for 24 hours. The reaction is cooled to room temperature and quenched by the addition of water. The mixture is partitioned between water and EtOAc (40 ml each), and the layers are shaken and separated. The aqueous layer is acidified to pH 3 with 1 N HCl and then extracted with EtOAc (40 ml). The combined organic layers are dried (anhydrous magnesium sulfate), filtered, concentrated, and flashed (100% EtOAc) to give the title compound as a cream solid (0.075 g, 34%). Mass (m/z): 399.2 (M⁺+1), 397.2 (M⁺−1).

Example 10

(3-Amino-5-chloro-2-cyclopropylcarbamoyl-4-methyl-thieno[2,3-b]pyridin-6-yloxy)-acetic acid (4-methyl-piperazin-1yl)-amide

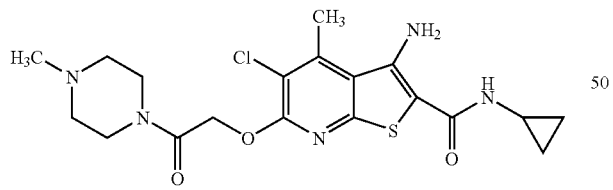

To a solution of (3-amino-5-chloro-2-cyclopropylcarbamoyl-4-methyl-thieno[2,3-b]pyridin-6-yloxy)-acetic acid (0.200 g, 0.562 mmol) in a 1:1 mixture of THF:DMF (1.5 ml each) are added 1-hydroxybenzotriazole hydrate (0.099 g, 0.731 mmol), N,N-diisopropylethylamine (0.109 g, 0.843 mmol), 1-[3-(dimethylamino)-propyl]-3-ethylcarbodiimide hydrochloride (0.162 g, 0.843 mmol), and N-methylpiperazine (0.169 g, 1.69 mmol). The resulting solution is stirred at room temperature for 24 hours, then at 50° C. for 24 hours. The reaction is cooled to room temperature and quenched by the addition of water. The mixture is partitioned between water and EtOAc (40 ml each), and the layers are shaken and separated. The aqueous layer is acidified to pH 3 with 1 N HCl and then extracted with EtOAc (40 ml). The combined organic layers are dried (anhydrous magnesium sulfate), filtered, concentrated, and flashed (100% EtOAc) to give the title compound as a yellow solid (0.080 g, 33%). Mass (m/z): 438.2 (M⁺+1), 436.2 (M⁺−1).

Example 11

3-Amino-5-chloro-6-(3-hydroxy-propoxy)-4-methyl-thieno[2,3-b]pyridine-2-carboxylic acid cyclopropylamide

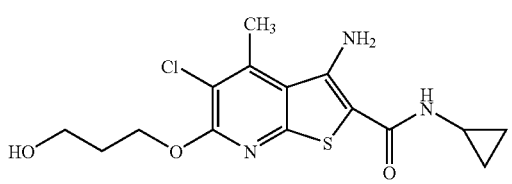

To a solution of 1,3-propanediol (1.053 g, 13.84 mmol) in THF (3 ml) at room temperature is added dropwise a solution of lithium bis(trimethylsilyl)amide (1.0 M in hexanes) (3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. for 1 hour, cooled to room temperature, and then quenched by the addition of water (15 ml). Ice is added to the reaction mixture and, while stirring, a yellow precipitate is formed. This solid is collected by filtration and placed in the vacuum oven to dry (60° C. for 16 hours). This affords the title compound as a yellow solid (0.240 g, 67%). Mass (m/z): 356.2 (M⁺+1), 354.1 (M⁺−1).

Example 12

3-Amino-5-chloro-6-[2-(2-hydroxy-ethoxy)-ethoxy]-4-methyl-thieno[2,3-b]pyridine-2-carboxylic acid cyclopropylamide

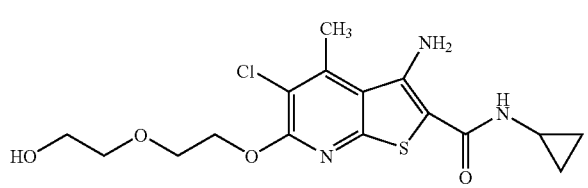

To a solution of diethylene glycol (1.118 g, 10.54 mmol) in THF (3 ml) at room temperature is added dropwise a solution of lithium bis(trimethylsilyl)amide (1.0 M in hexanes) (3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. for 1 hour, cooled to room temperature, and then quenched by the addition of water (15 ml). Ice is added to the reaction mixture and, while stirring, a yellow precipitate is formed. This solid is collected by filtration and placed in the vacuum oven to dry (60° C. for 16 hours). This affords the title compound as a yellow solid (0.150 g, 39%). Mass (m/z): 386.2 (M++1), 384.1 (M+−1).

Example 13

3-Amino-5-chloro-6-[2-(2-hydroxy-ethyamino)-ethoxy]-4-methyl-thieno[2,3-b]pyridine-2-carboxylic acid cyclopropylamide

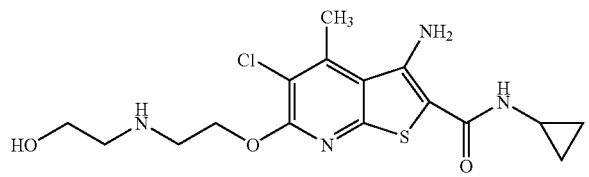

To a solution of diethanolamine (1.097 g, 10.43 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. for 1 hour, cooled to room temperature, and then quenched by the addition of water (15 ml). Ice is added to the reaction mixture and, while stirring, a yellow precipitate is formed. This solid is collected by filtration and placed in the vacuum oven to dry (60° C. for 16 hours). This affords the title compound as a yellow solid (0.216 g, 56%). Mass (m/z): 385.2 (M+ +1), 383.1 (M+−1).

Example 14

3-Amino-5-chloro-4-methyl-6-(2-piperazin-1-yl-ethoxy)-thieno[2,3-b]pyridine-2-carboxylic acid cyclopropylamide

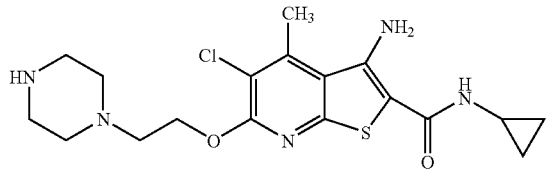

To a solution of 1-(2-hydroxyethyl)piperazine (1.061 g, 8.15 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. for 1 hour, cooled to room temperature, and then quenched by the addition of water (15 ml). Ice is added to the reaction mixture and, while stirring, a yellow precipitate is formed. This solid is collected by filtration and placed in the vacuum oven to dry (60° C. for 16 hours). This affords the title compound as a yellow solid (0.245 g, 71%). Mass (m/z): 410.2 (M++1), 408.2 (M+−1).

Example 15

3-Amino-5-chloro-4-methyl-6-(2-methylsulfanyl-ethoxy)-thieno[2,3-b]pyridine-2-carboxylic acid cyclopropylamide

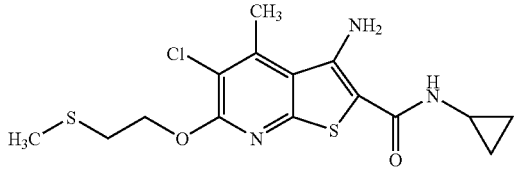

To a solution of 2-(methylthio)ethanol (1.060 g, 11.50 mmol) in THF (3 ml) at room temperature is added dropwise a solution of lithium bis(trimethylsilyl)amide (1.0M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 80° C. in a sealed tube for 1.5 hours, cooled to room temperature, and then quenched by the addition of water (15 ml). Ice is added to the reaction mixture and, while stirring, a yellow precipitate is formed. This solid is collected by filtration and placed in the vacuum oven to dry (60° C. for 16 hours). This affords the title compound as a yellow solid (0.203 g, 55%). Mass (m/z): 372.1 (M++1), 370.1 (M+−1).

Example 16

3-Amino-5-chloro-4-methyl-6-[2-(2-piperazin-1-yl-ethoxy)-ethyl]-thieno[2,3-b]pyridine-2-carboxylic acid cyclopropylamide

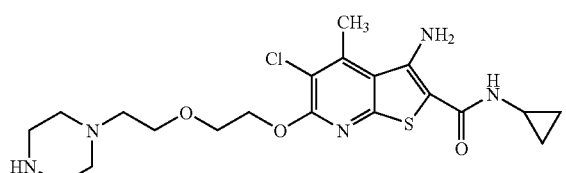

To a solution of 1-[2-(2-hydroxyethoxy)ethyl]piperazine (1.061 g, 6.09 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 80° C. in a sealed tube for 1.5 hours, cooled to room temperature, and then quenched by the addition of water (15 ml). Ice is added to the reaction mixture and, while stirring, a yellow precipitate forms. This solid is collected by filtration and placed in

Example 17

6-(2-Acetylamino-ethoxy)-3-amino-5-chloro-4-methyl-thieno[2,3-b]pyridine-2-carboxylic acid cyclopropylamide

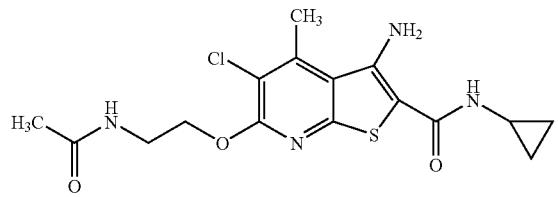

To a solution of N-acetylethanolamine (1.120 g, 10.86 mmol) in THF (3 ml) at room temperature is added dropwise a solution of lithium bis(trimethylsilyl)amide (1.0 M in hexanes) (3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 80° C. in a sealed tube for 1.5 hours, cooled to room temperature, and then quenched by the addition of water (15 ml). Ice is added to the reaction mixture and, while stirring, a yellow precipitate is formed. This solid is collected by filtration and placed in the vacuum oven to dry (60° C. for 16 hours). This affords the title compound as a yellow solid (0.199 g, 52%). Mass (m/z): 383.2 (M$^+$+1), 381.1 (M$^+$−1).

Example 18

3-Amino-5-chloro-4-methyl-6-(3-pyridin-2-yl-propoxy)-thieno[2,3-b]pyridine-2-carboxylic acid cyclopropylamide

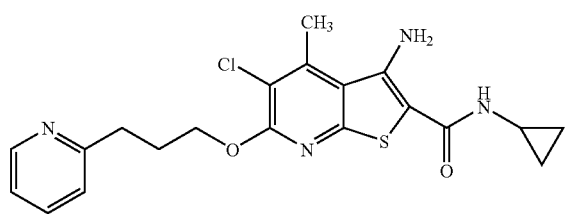

To a solution of 2-pyridinepropanol (0.960 g, 7.0 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. in a sealed tube for 1.5 hours, cooled to room temperature, and then quenched by the addition of water (10 ml). The reaction mixture is transferred to an erlenmeyer flask and diluted to 75 ml with water. The mixture is cooled to 0° C. and stirred. During this time, a yellow precipitate is formed. This solid is collected by filtration and slurried in a 2:1 EtOAc:hexane mixture. This slurry is stirred for 10 minutes, filtered, and the collected solid is placed in the vacuum oven to dry (60° C. for 16 hours). This affords the title compound as a yellow solid (0.141 g, 34%). Mass (m/z): 417.2 (M$^+$+1), 415.1 (M$^+$−1).

Example 19

3-Amino-5-chloro-4-methyl-6-(3-pyridin-3-yl-propoxy)-thieno[2,3-b]pyridine-2-carboxylic acid cyclopropylamide

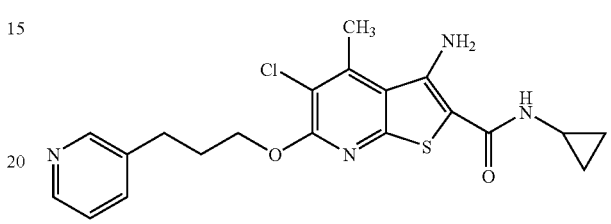

To a solution of 3-pyridinepropanol (0.960 g, 7.0 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. in a sealed tube for 1.5 hours, cooled to room temperature, and then quenched by the addition of water (10 ml). The reaction mixture is transferred to an erlenmeyer flask and diluted to 75 ml with water. The mixture is cooled to 0° C. and stirred. During this time, a yellow precipitate is formed. This solid is collected by filtration and slurried in a 2:1 EtOAc:hexane mixture. This slurry is stirred for 10 minutes, filtered, and the collected solid is placed in the vacuum oven to dry (60° C. for 16 hours). This affords the title compound as a yellow solid (0.242 g, 58%). Mass (m/z): 417.2 (M$^+$+1), 415.2 (M$^+$−1).

Example 20

3-Amino-5-chloro-4-methyl-6-(2-pyridin-4-yl-ethoxy)-thieno[2,3-b]pyridine-2-carboxylic acid cyclopropylamide

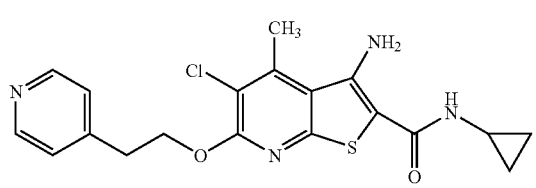

To a solution of 4-pyridineethanol (0.862 g, 7.0 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. in a sealed tube for 1.5 hours, cooled to room temperature, and then quenched by the addition of water (10 ml). The reaction mixture is transferred to an erlenmeyer flask and diluted to 75 ml with water. The mixture is cooled to 0° C. and stirred. During this time, a yellow precipitate is formed. This solid is collected by filtration and slurried in a 2:1 EtOAc:hexane mixture. This slurry is stirred for 10 minutes, filtered, and the collected solid is placed in the vacuum oven to dry (60° C. for 16 hours). This affords the title compound as a yellow solid (0.231 g, 57%). Mass (m/z): 403.1 ($M^+$+1), 401.1 ($M^+$−1).

Example 21

3-Amino-6-{2-[bis-(2-hydroxyethyl)-amino]-ethoxy}-5-chloro-4-methyl-thieno[2,3-b]pyridine-2-carboxylic acid cyclopropylamide

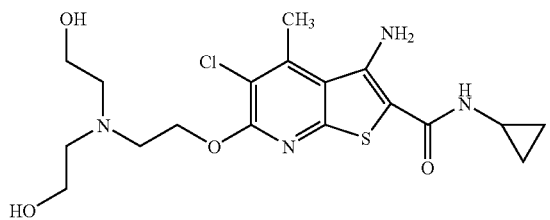

To a solution of triethanolamine (1.044 g, 7.0 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. in a sealed tube for 1.5 hours, cooled to room temperature, and then quenched by the addition of water (10 ml). The reaction mixture is transferred to an erlenmeyer flask and diluted to 75 ml with water. The mixture is cooled to 0° C. and stirred. During this time, a yellow precipitate is formed. This solid is collected by filtration and slurried in a 2:1 EtOAc:hexane mixture. This slurry is stirred for 10 minutes, filtered, and the collected solid is placed in the vacuum oven to dry (60° C. for 16 hours). This affords the title compound as a yellow solid (0.179 g, 41%). Mass (m/z): 429.2 ($M^+$+1), 427.2 ($M^+$−1).

Example 22

3-Amino-5-chloro-6-([1,3]dioxolan-4-ylmethoxy)-4-methyl-thieno[2,3-b]pyridine-2-carboxylic acid cyclopropylamide

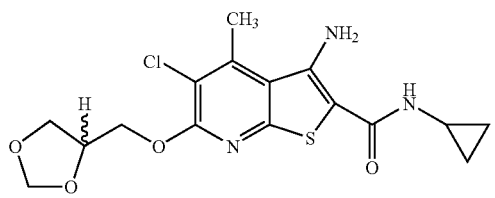

To a solution of glycerol formal (0.729 g, 7.0 mmol) in THF (3 ml) at room temperature is added dropwise a solution of lithium bis(trimethylsilyl)amide (1.0 M in hexanes)(3.50 ml, 3.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 75° C. in a sealed tube for 1.5 hours, cooled to room temperature, and then quenched by the addition of water (10 ml). The reaction mixture is transferred to an erlenmeyer flask and diluted to 75 ml with water. The mixture is cooled to 0° C. and stirred. During this time, a white precipitate is formed. This solid is collected by filtration and slurried in a 2:1 EtOAc:hexane mixture. This slurry is stirred for 10 minutes, filtered, and the collected solid is placed in the vacuum oven to dry (60° C. for 16 hours). This affords the title compound as a white solid (0.195 g, 51%). Mass (m/z): 384.1 ($M^+$+1), 382.1 ($M^+$−1).

Example 23

3-Amino-5-chloro-4-methyl-6-[(2-pyrrolidin-1-yl-ethylcarbamoyl)-methoxy]-thieno[2,3-b]pyridine-2-carboxylic acid cyclopropylamide

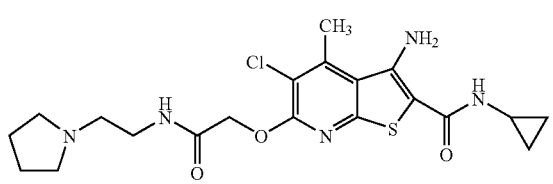

To a solution of (3-amino-5-chloro-2-cyclopropylcarbamoyl-4-methyl-thieno[2,3-b]pyridin-6-yloxy)-acetic acid (0.300 g, 0.843 mmol) in a 1:1 mixture of THF:DMF (2.0 ml each) are added 1-hydroxybenzotriazole hydrate (0.148 g, 1.096 mmol), N,N-diisopropylethylamine (0.163 g, 1.265 mmol), 1-[3-(dimethylamino)propyl]-3-ethylcarbodiimide hydrochloride (0.242 g, 1.265 mmol), and 1-(2-aminoethyl)pyrrolidine (0.289 g, 2.529 mmol). The resulting solution is stirred at room temperature for 16 hours. The reaction is quenched by the addition of water (25 ml). A yellow precipitate formed. The mixture is cooled to 0° C. and stirred for 10 minutes, then filtered. The collected solid is dried in the vacuum oven for 3 hours at 60° C. This affords the title compound as a yellow solid (0.069 g, 18%). Mass (m/z): 452.2 ($M^+$+1), 450.2 ($M^+$−1).

Example 24

3-Amino-5-chloro-6-[(4-fluoro-benzylcarbamoyl)-methoxy]-4-methyl-thieno[2,3-b]pyridine-2-carboxylic acid cyclopropylamide

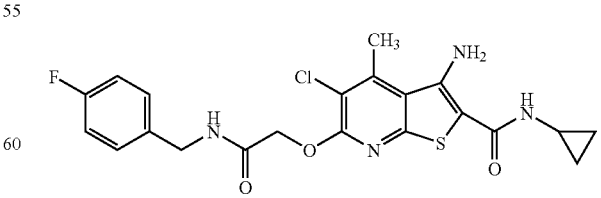

To a solution of (3-amino-5-chloro-2-cyclopropylcarbamoyl-4-methyl-thieno[2,3-b]pyridin-6-yloxy)-acetic acid (0.300 g, 0.843 mmol) in a 1:1 mixture of THF:DMF (2.0 ml each) are added 1-hydroxybenzotriazole hydrate (0.148 g, 1.096 mmol), N,N-diisopropylethylamine (0.163 g, 1.265 mmol), 1-[3-(dimethylamino)propyl]-3-ethylcarbodiimide hydrochloride (0.242 g, 1.265 mmol), and 4-fluorobenzylamine (0.317 g, 2.529 mmol). The resulting solution is stirred at room temperature for 16 hours. The reaction is quenched by the addition of water (25 ml). A yellow precipitate is formed. The mixture is cooled to 0° C. and stirred for 10 minutes, then filtered. The collected solid is slurried in 10:1 hexane:EtOAc and stirred for 10 minutes. The solid is collected by filtration and dried in the vacuum oven at 50° C. for 1 hour. This affords the title compound as a pale yellow solid (0.143 g, 37%). Mass (m/z): 463.1 (M$^+$+1), 461.1 (M$^+$−1).

Example 25

3-Amino-5-chloro-4-methyl-6-[(2-morpholin-4-yl-ethylcarbamoyl)-methoxy]-thieno[2,3-b]pyridine-2-carboxylic acid cyclopropylamide

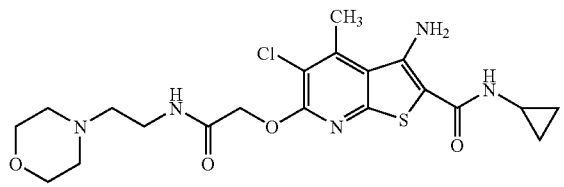

To a solution of (3-amino-5-chloro-2-cyclopropylcarbamoyl-4-methyl-thieno[2,3-b]pyridin-6-yloxy)-acetic acid (0.300 g, 0.843 mmol) in a 1:1 mixture of THF:DMF (2.0 ml each) are added 1-hydroxybenzotriazole hydrate (0.148 g, 1.096 mmol), N,N-diisopropylethylamine (0.163 g, 1.265 mmol), 1-[3-(dimethylamino)propyl]-3-ethylcarbodiimide hydrochloride (0.242 g, 1.265 mmol), and 4-(2-aminoethyl)morpholine (0.329 g, 2.529 mmol). The resulting solution is stirred at room temperature for 16 hours. The reaction is quenched by the addition of water (25 ml). If no precipitate forms, the mixture may be acidified to pH2 with 1 N HCl and extracted with EtOAc (25 ml). The organic layer is discarded and the aqueous layer is made basic (pH12) with 5N NaOH and extracted with EtOAc (40 ml). The organic layer is dried (anhydrous magnesium sulfate), filtered, and concentrated to give a yellow solid. The solid is slurried in 3:1 hexane:EtOAc (10 ml), then filtered. The collected solid is dried in the vacuum oven at 50° C. for 72 hours. This affords the title compound as a yellow solid (0.053 g, 13%). Mass (m/z): 468.2 (M$^+$+1), 466.2 (M$^+$−1).

Example 26

3-amino-5-chloro-4-methyl-6-{2-[(pyridine-4-carbonyl)-amino]-ethoxy}-thieno[2,3-b]pyridine-2-carboxylic acid cyclopropylamide

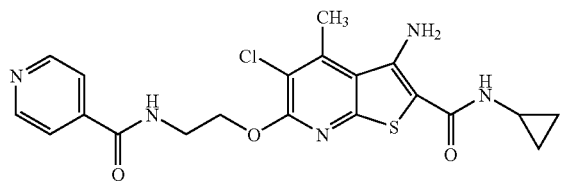

To a solution of N-(2-hydroxyethyl)-isonicotinamide (0.831 g, 5.00 mmol) in THF (2.5 ml) at room temperature is added dropwise a solution of lithium bis(trimethylsilyl)amide (1.0 M in hexanes)(2.50 ml, 2.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 80° C. in a sealed tube for 2 hours, cooled to room temperature, and then quenched by the addition of water (15 ml). The mixture is diluted to 100 ml with water and then cooled to 0° C. and stirred. A yellow precipitate is formed. This solid is collected by filtration, slurried in EtOAc, and filtered again to give a yellow solid which is placed in the vacuum oven to dry (50° C. for 3 hours). This affords the title compound as a yellow solid (0.046 g, 10%). Mass (m/z): 446.3 (M++1), 444.2 (M$^+$−1).

Example 27

3-Amino-6-benzyloxy-5-chloro-4-methyl-thieno[2,3-b]pyridine-2-carboxylic acid cyclopropylamide

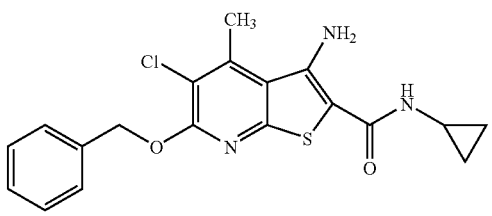

To a solution of benzyl alcohol (0.541 g, 5.00 mmol) in THF (2.5 ml) at room temperature is added dropwise a solution of lithium bis(trimethylsilyl)amide (1.0 M in hexanes) (2.50 ml, 2.50 mmol). The reaction mixture is stirred for 15 minutes and then is treated with 3-amino-5-chloro-6-methanesulfinyl-4-methyl-thieno[2,3-b]pyridine-2-carboxylic acid cyclopropylamide (0.345 g, 1.00 mmol). The reaction mixture is heated at 80° C. in a sealed tube for 2 hours, cooled to room temperature, and then quenched by the addition of water (15 ml). The mixture is diluted to 100 ml with water and then cooled to 0° C. and stirred. A yellow precipitate is formed. This solid is collected by filtration and purified by flash chromatography (1.5:1 hexane:EtOAc) to give the title compound as a pale yellow solid (0.130 g, 33%). Mass (m/z): 388.2 (M$^+$+1), 386.2 (M$^+$−1).

Example 28

3-Amino-5-chloro-4-methyl-6-(2-morpholin-4-yl-ethoxy)-thieno[2,3-b]pyridine-2-carboxylic acid cyclopropylamide hydrochloride

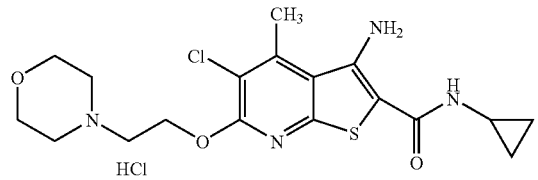

A mixture of 3-amino-5-chloro-4-methyl-6-(2-morpholin-4-yl-ethoxy)-thieno[2,3-b]pyridine-2-carboxylic acid cyclopropylamide (0.800 g, 1.95 mmol) and MeOH (50 ml) is heated to 50° C. The mixture is treated with THF (5 ml) and DMF (5 ml). While still at 50° C., the mixture is acidified to pH1 with concentrated HCl. A homogeneous solution is formed. The solution is allowed to cool slowly to room temperature. During this time, a white precipitate is formed. This solid is collected by filtration and dried in the vacuum oven for 72 hours at 50° C. This affords the title compound as a white solid (0.562 g, 65%). Mass (m/z): 411.1 ($M^+$+1)-HCl, 445.1 ($M^+$−1).

Example 29

3-Amino-5-chloro-6-ethoxy-4-methyl-thieno[2,3-b]pyridine-2-carboxylic acid cyclopropylamide

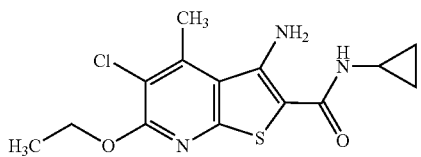

Sodium hydride (0.037 g, 0.925 mmol) is suspended in anhydrous 1,2-dimethoxy-ethane (5.0 ml) under nitrogen. The suspension is cooled to 0° C. To this cold suspension is added via cannula a solution of 3-amino-5-chloro-6-hydroxy-4-methyl-thieno[2,3-b]pyridine-2-carboxylic acid cyclopropylamide (0.300 g, 1.01 mmol) in anhydrous DMF (5.0 ml). The ice bath is removed, and the reaction is warmed to room temperature. After the reaction is stirred 25 minutes at room temperature, lithium bromide (0.175 g, 2.02 mmol) is added as a solid, and the reaction is stirred for an additional two hours. Finally, ethyl iodide is added (0.24 ml, 0.47 g, 3.00 mmol), and the reaction is stirred for 36 hours at room temperature. At the completion of the reaction time, the mixture is quenched with water. The solid is collected by filtration, then purified by flash chromatography (hexanes:EtOAc gradient) to give the title compound as a white solid (24.3 mg, 8% yield). Mass (m/z): 326.0 ($M^+$), 324.0 ($M^-$).

Alternatively, Example 33 may be prepared following the procedures outlined for the preparation of Example 29, substituting EtOH for benzyl alcohol.

Example 30

(3-Amino-5-chloro-2-cyclopropylcarbamoyl-4-methyl-thieno[2,3-b]pyridin-6-yloxy)-acetic acid (imidazol-1-yl)-amide

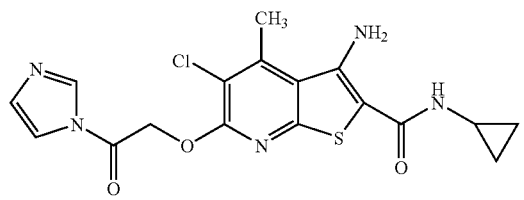

To a solution of (3-amino-5-chloro-2-cyclopropylcarbamoyl-4-methyl-thieno[2,3-b]pyridin-6-yloxy)-acetic acid (0.350 g, 0.98 mmol) in DMF (4 ml) at room temperature is added 1,1'-carbonyldiimidazole (0.239 g, 1.48 mmol). The resulting solution is heated and stirred at 40° C. for 20 minutes. During this time, a cream colored precipitate is formed. The mixture is cooled to 10° C., and neat 2-aminopyridine (0.231 g, 2.46 mmol) is added. The mixture is stirred at room temperature for 30 minutes, then quenched by adding saturated sodium bicarbonate solution (10 ml). A thick, white precipitate is formed. The mixture is diluted with water (25 ml), stirred for 10 minutes, then filtered. The collected solid is dried in the vacuum oven for 16 hours. This affords the title compound as a white solid (0.228 g, 58%). Mass (m/z): 404.0 ($M^+$−1).

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

Thus, the present invention provides pharmaceutical compositions comprising a compound of the Formula I and a pharmaceutically acceptable diluent.

The compounds of Formula I can be administered by a variety of routes. In effecting treatment of a patient afflicted with disorders described herein, a compound of Formula I can be administered in any form or mode that makes the compound bioavailable in an effective amount, including oral and parenteral routes. For example, compounds of Formula I can be administered orally, by inhalation, or by the subcutaneous, intramuscular, intravenous, transdermal, intranasal, rectal, occular, topical, sublingual, buccal, or other routes. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.001% of a compound of the invention, but may be varied to be between 0.001 and about 90% of the weight thereof. The amount of the compound of Formula I present in such compositions is such that a suitable dosage will be obtained. The solutions or suspensions may also include one or more of the following adjuvants: sterile diluents, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diamine-tetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so, the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of a compound of Formula I or its pharmaceutical salt from about 0.1 to about 10% w/v (weight per unit volume).

The compounds of Formula I are allosteric potentiators of the $M_4$ subtype of muscarinic receptors. Furthermore, the compounds of Formula I selectively potentiate $M_4$ receptors relative to other muscarinic receptors. The activity of the compounds of the present invention may be determined by the methods below.

Calcium Mobilization in Whole Cells Stably Expressing Human Muscarinic Receptors A. Stable Cell Lines Standard molecular cloning techniques may be used to generate stable cell lines expressing the human muscarinic $M_1$-$M_5$ receptors. $M_1$, $M_3$ an $M_5$ receptors are expressed in chinese hamster ovary (CHO) cell lines, whereas, $M_2$ an $M_4$ are expressed in AV12 $G_{\alpha15}$ cell lines. The cDNA encoding these muscarinic receptors correspond to the published sequence in the NCBI nucleotide database of accession numbers: AF498915, AF498916, AF498917, AF498918 and AF498919, for $M_1$-$M_5$ respectively.

B. Methods

Using a calcium-sensitive fluorescent dye, agonist or potentiation activity of a given compound can be detected in a single assay using a Fluorescence Light Imaging Plate Reader (FLIPR) instrument. Cells are plated in Poly-D-Lysine coated black plates/clear bottom (Becton Dickinsons) at 40,000 cells per ml (100 µl/well) in growth media 24 hours prior to running the assay. The medium is removed before the addition of 50 µl fluorescence dye solution (HBSS containing 20 mM Hepes, 10 µM Fluo-3-AM, 0.05% pluronic acid F127; supplemented with 2.5 mM probenecid for CHO cell assays). The cells are incubated with the dye for 75 minutes before replacing with assay buffer (20 mM Hepes in Hanks balanced salt solution (Gibco); supplemented with 2.5 mM probenecid for CHO cells). The plate is transferred to the FLIPR machine (Molecular Devices) for fluorescence recordings. The cells are periodically excited by 488 nm light, and the emitted fluorescent light passed through a 510-570 nm filter and then detected by a cooled CCD camera. Automated multiple compound additions are timed by computer program. Cells are pre-incubated with increasing concentration of compounds. After 2 minutes, a range of acetylcholine concentrations is added to each concentration of compound. If the compound is an allosteric enhancer, a compound concentration-dependent potentiation of acetylcholine response would be detectable. The effectiveness of potentiator compounds can be ranked by their affinity and cooperativity.

An alternative method may be used to provide an estimate of the affinity of compounds of the present invention, and to rank order the compounds based on this estimated affinity. In this method, a single concentration of carbachol that is approximately 10% of a saturating concentration is added to all wells, and increasing concentrations of the test compounds of the present invention are added. An estimated affinity value is derived by calculation of the $EC_{50}$ for potentiation of the 10% carbachol response. This method may be used to rank order the compounds described herein as Examples.

As confirmed with the compound of Example 1, acetylcholine and carbachol (both non-selective full muscarinic receptor agonists) are potentiated in an equivalent fashion in the presence of an allosteric modulator.

C. Data Analysis and Results

Allosteric parameters may be estimated using the equations by Lazareno et al., *Mol. Pharmacol.* (1995) 48: 362-378. The effect of increasing concentrations of the compound of Example 1 on cellular ACh concentration-response curves in recombinant cell lines (AV12 $G_{\alpha15}$ $hM_2$ or $hM_4$ and CHO $hM_1$, $hM_3$ or $hM_5$) may be tested using FLIPR. Data are collected in duplicates from at least three independent experiments. No significant allosteric effect is observed in CHO cells stably expressing $hM_1$, $hM_3$ or $hM_5$ receptors. The cooperatively factor and affinity of the compound of Example 1 for $hM_4$ receptors is estimated to be 34.5±3.5 and 200±42 nM, respectively. A modest allosteric effect on $hM_2$ receptors is also observed but is too modest to be accurately estimated.

Using the FLIPR assay to potentiate 10% carbachol, as described above for rank ordering of the compounds of the present invention, each of the compounds described herein as EXAMPLES has an estimated affinity for $hM_4$ receptors of <500 nM.

Neurotransmitter Release Assay

A. Methods

Two male Lister Hooded rats are killed by carbon dioxide asphyxiation and cervical dislocation. The brains are rapidly removed, and the striatum dissected out and cross-chopped three times at 150 μm. The slices are suspended in 12 ml of HEPES buffer (128 mM NaCl, 2.4 mM KCl, 3.2 mM $CaCl_2$, 1.2 mM $KH_2PO_4$, 1.2 mM $MgSO_4 7H_2 0$, 25 mM HEPES, 10 mM Glucose, pH 7.5). The slices are washed twice, with resuspending in fresh buffer each time, then incubated at 37° C. for 30 minutes with [$^3$H]-choline chloride (250 nM). After 30 minutes, a further four washes are carried out, and 100 μl of slices are placed in each well of a 96 well filter plate (Millipore MABCN 96-well multiscreen plate). The bathing solution is removed by vacuum filtration (Millipore Univac manifold system), then a further 70 μl of HEPES buffer (+/− compound) is added to each well, and the plate is returned to the incubator for 5 minutes. After a 5-minute incubation, the buffer is removed by vacuum filtration into a collecting plate (Wallac 96 well flexible sample plates). Stimulating solution (70 μl/well: 20 mM potassium+/− compound) is then added, and the plate returned to the incubator for a further 5-minutes. The stimulating buffer is then removed by vacuum filtration into a second collecting plate. At the end of the experiment, the amount of tissue in each well is estimated by placing the plates in a freezer for one hour, punching out the filter discs, and adding Soluene® (to digest the slices) and leaving for a further hour. The radioactivity in the digested tissue is measured using liquid scintillation counting. Neurotransmitter release is calculated as a fraction of total radioactivity present in the well.

B. Results

The potentiation effect of compounds in native tissues is tested by its ability to potentiate auto-inhibition of acetylcholine release in striatal slices, as induced by 20 mM potassium stimulation. This i's considered to be an $M_4$-mediated process via pre-synaptic auto-regulation in the striatum. Zhang, W. et al., *J. Neurosci.* (2002) 22: 1709-1717. Using the methods above, a representative compound of the present invention (Example 1) exhibits concentration-dependent potentiation of auto-inhibition with an $IC_{50}$ of 1.5 μM.

Several preclinical laboratory animal models have been described for a number of the disorders associated with muscarinic receptors. For instance, inhibition of the conditioned avoidance response (CAR) by neuroleptic and atypical antipsychotics is one of the most studied pharmacological models of psychosis. To date, all clinically effective antipsychotics have been demonstrated to selectively suppress CAR (cf. Wadenberg & Hicks, 1999. *Neuroscience & Biobehavioral Reviews*, 23: 851-8).

Conditioned Avoidance Response

A. Methods

Male Fisher-344 rats (N=5-8) are trained in an avoidance paradigm in which the rat must make a shuttle response to avoid or escape a footshock. The apparatus is a Coulbourn Instruments shuttle operant chamber. Each session equals a total of 50 trials, presented on a 30 second inter-trial interval, and each trial begins with simultaneous illumination of a houselight and rising of a guillotine door. The rat is given 10 seconds to cross over to the other side (an avoidance response) before a 1 mA footshock is initiated. The shock remains on until the rat crosses over to the other side (an escape response) or 10 seconds has elapsed (an escape failure). Rats are well trained on this task, with baseline avoidance performance >95%. The number of avoidance, escape and escape failure responses during each session is recorded and used for analysis.

Groups of rats are dosed with (1) vehicle (10% acacia plus sterile water), (2) a sub-efficacious dose of the muscarinic agonist oxotremorine sesquifumarate (Oxo alone), or (3) Oxo in the presence of increasing doses of the test compound (10 mg/kg to 60 mg/kg), followed by (4) a retest of Oxo alone. Each test compound is administered orally 2 hours prior to testing. Oxo (0.03 mg/kg) is administered subcutaneously 30 minutes prior to testing. Data are analyzed via a one-way (within-group design) Analysis of Variance (ANOVA). In cases of a significant ANOVA (p<0.05), post-hoc comparisons may be made in which compound doses are compared back to the Oxo alone group (paired t-test).

B. Results

| Example Number | Percent Avoidance Response (Mean ± S.E.M.) | | | | | |
|---|---|---|---|---|---|---|
| | Vehicle | Oxo alone | Oxo + Test Compound | | | Oxo alone |
| | | | 10 mg/kg | 30 mg/kg | 60 mg/kg | |
| 1 | 97 ± 1.6 | 93 ± 1.8 | 46* ± 7.4 | 11* ± 1.9 | NT | 91 ± 0.9 |
| 6 | 96 ± 1.2 | 93 ± 1.2 | 90 ± 3.4 | 54* ± 10.2 | NT | 90 ± 2.5 |
| 10 | 97 ± 1.2 | 89 ± 3.8 | 85 ± 5.3 | 54* ± 7.6 | 48* ± 14.1 | 89 ± 3.2 |
| 28 | 96 ± 1.5 | 92 ± 1.5 | NT | 84 ± 6.3 | 61* ± 16.1 | 91 ± 2.0 |

The conditioned avoidance assay is highly predictive of antipsychotic efficacy in the clinic. Representative muscarinic $M_4$ receptor potentiators exhibit an antipsychotic-like profile in the conditioned avoidance responding paradigm. Although these $M_4$ potentiators are inactive when tested alone (data not shown), these compounds potentiate the efficacy of an inactive dose of the muscarinic agonist oxotremorine.

The results of calcium mobilization and neurotransmitter release studies demonstrate the ability of compounds of the present invention to act as potentiators of $M_4$ muscarinic receptors. It is recognized that the compounds of the present invention would be expected to potentiate the effects of $M_4$ receptor activation. Thus, the compounds of the present invention are expected to be useful in the treatment of various disorders associated with muscarinic receptors, as described to be treated herein, and other disorders that can be treated by such allosteric potentiators, as are appreciated by those skilled in the art.

The disorders associated with $M_4$ muscarinic receptors are treated by administering an effective amount of a compound or pharmaceutical composition of Formula I. An effective amount can be readily determined by the attending diagnostician, as one skilled in the art, by the use of conventional techniques and by observing results obtained under analogous circumstances. In determining an effective amount, the dose of a compound of Formula I, a number of factors are considered by the attending diagnostician, including, but not limited to: the compound of Formula I to be administered; the species of mammal—its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.001 milligram per kilogram of body weight per day (mg/kg/day) to about 100 mg/kg/day. Preferred amounts may be readily determined by one skilled in the art.

What is claimed is:

1. A compound of Formula I:

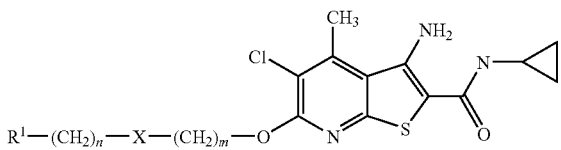

wherein:
m is 1, or 2;
n is 0, 1, or 2;
X is a bond, —O—, —$SO_p$—, —C(O)—, —$NR^2$—, —C(O)—$NR^2$—, or —$NR^2$—C(O)—;
p is 0, 1, or 2;
$R^1$ is hydrogen, hydroxyl, $C_1$-$C_4$ alkyl, phenyl, pyridyl, pyrrolidinyl, piperazinyl, morpholino, thiazolyl, imidazolyl, or 1,3-dioxalanyl;
which phenyl, piperazinyl, or thiazolyl group may be optionally substituted with one substituent selected from the group consisting of halo or $C_1$-$C_2$ alkyl;
wherein n cannot be 0 when p is 0, or when X is —O—, —$NR^2$, or —$NR^2$—C(O)—;
$R^2$ is hydrogen or $C_1$-$C_2$ alkyl;
which $C_1$-$C_2$ alkyl may be optionally substituted with one hydroxyl;
or a pharmaceutically acceptable salt thereof.

2. The compound of claim 1 wherein X is a bond.
3. The compound of claim 2 wherein n is 0.
4. The compound of claim 2 wherein m is 1.
5. The compound of claim 2 wherein $R^1$ is hydrogen.
6. The compound of claim 2 wherein m is 2.
7. The compound of claim 2 wherein $R^1$ is morpholino.
8. The compound of claim 1 which is 3-amino-5-chloro-6-methoxy-4-methyl-thieno[2,3-b]pyridine-2-carboxylic acid cyclopropylamide, or a pharmaceutically acceptable salt thereof.
9. The compound of claim 1 which is 3-amino-5-chloro-4-methyl-6-(2-morpholin-4-yl-ethoxy)-thieno[2,3-b]pyridine-2-carboxylic acid cyclopropylamide, or a pharmaceutically acceptable salt thereof.
10. A compound which is 3-Amino-5-chloro-6-hydroxy-4-methyl-thieno[2,3-b]pyridine-2-carboxylic acid cyclopropylamide or 3-Amino-5-chloro-6-isopropoxy-4-methyl-thieno[2,3-b]pyridine-2-carboxylic acid cyclopropylamide, or a pharmaceutically acceptable salt thereof.
11. A pharmaceutical composition comprising the compound of claim 1, or a pharmaceutically acceptable salt thereof, in combination with a pharmaceutically acceptable carrier, excipient, or diluent.

* * * * *

UNITED STATES PATENT AND TRADEMARK OFFICE
CERTIFICATE OF CORRECTION

PATENT NO. : 8,071,776 B2
APPLICATION NO. : 11/577508
DATED : December 6, 2011
INVENTOR(S) : Almudena Rubio Esteban et al.

It is certified that error appears in the above-identified patent and that said Letters Patent is hereby corrected as shown below:

On the title page, item [56]; Col. 2 (Other Publications) Line 15: Delete "mechamisms" and insert -- mechanisms --, therefor.

At Column 33, Line 33: In Claim 1, delete "1,3-dioxalanyl;" and insert -- 1,3-dioxolanyl; --, therefor.

At Column 34, Line 23: In Claim 10, delete "Amino" and insert -- amino --, therefor.

At Column 34, Line 25: In Claim 10, delete "Amino" and insert -- amino --, therefor.

Signed and Sealed this
Third Day of April, 2012

David J. Kappos
*Director of the United States Patent and Trademark Office*